(12) United States Patent
Frangioni

(10) Patent No.: US 7,794,394 B2
(45) Date of Patent: Sep. 14, 2010

(54) DEVICE FOR WAVELENGTH-SELECTIVE IMAGING

(75) Inventor: John V. Frangioni, Wayland, MA (US)

(73) Assignee: Beth Israel Deaconess Medical Center, Boston, MA (US)

(*) Notice: Subject to any disclaimer, the term of this patent is extended or adjusted under 35 U.S.C. 154(b) by 1390 days.

(21) Appl. No.: 10/517,280

(22) PCT Filed: May 22, 2003

(86) PCT No.: PCT/US03/16285

§ 371 (c)(1),
(2), (4) Date: Jun. 24, 2005

(87) PCT Pub. No.: WO03/100925

PCT Pub. Date: Dec. 4, 2003

(65) Prior Publication Data

US 2005/0285038 A1  Dec. 29, 2005

Related U.S. Application Data

(60) Provisional application No. 60/382,524, filed on May 22, 2002.

(51) Int. Cl.
*A61B 1/06* (2006.01)
(52) U.S. Cl. ........................ 600/160; 600/431; 250/226
(58) Field of Classification Search .................. 250/330, 250/226, 208.1, 214.1; 600/109, 160, 178, 600/407, 476, 478, 473; 257/440, 458, 463
See application file for complete search history.

(56) References Cited

U.S. PATENT DOCUMENTS

| 4,238,760 | A | | 12/1980 | Carr |
| 4,807,026 | A | | 2/1989 | Nishioka et al. |
| RE34,411 | E | | 10/1993 | Nishioka et al. |
| 5,474,910 | A | | 12/1995 | Alfano |
| 5,701,903 | A | * | 12/1997 | Sano et al. .................. 600/478 |
| 5,965,875 | A | | 10/1999 | Merrill |
| 6,061,591 | A | | 5/2000 | Freitag et al. |
| 6,133,953 | A | * | 10/2000 | Okada ........................ 348/272 |
| 6,198,147 | B1 | * | 3/2001 | Connolly .................... 257/461 |

(Continued)

FOREIGN PATENT DOCUMENTS

EP   177761   2/2002

(Continued)

*Primary Examiner*—Long V Le
*Assistant Examiner*—Nicholas L Evoy
(74) *Attorney, Agent, or Firm*—Strategic Patents, P.C.

(57) ABSTRACT

An imaging device captures both a visible light image and a diagnostic image, the diagnostic image corresponding to emissions from an imaging medium within the object. The visible light image (which may be color or grayscale) and the diagnostic image may be superimposed to display regions of diagnostic significance within a visible light image. A number of imaging media may be used according to an intended application for the imaging device, and an imaging medium may have wavelengths above, below, or within the visible light spectrum. The devices described herein may be advantageously packaged within a single integrated device or other solid state device, and/or employed in an integrated, single-camera medical imaging system, as well as many non-medical imaging systems that would benefit from simultaneous capture of visible-light wavelength images along with images at other wavelengths.

20 Claims, 4 Drawing Sheets

U.S. PATENT DOCUMENTS

| | | |
|---|---|---|
| 6,293,911 B1 * | 9/2001 | Imaizumi et al. ............ 600/160 |
| 6,455,908 B1 * | 9/2002 | Johnson et al. ............. 257/440 |
| 2002/0049386 A1 | 4/2002 | Muller et al. |

FOREIGN PATENT DOCUMENTS

| | | |
|---|---|---|
| EP | 1177761 A2 | 2/2002 |
| WO | WO-02/27804 | 4/2002 |
| WO | WO-2005/079662 | 9/2005 |

* cited by examiner

DEVICE FOR WAVELENGTH-SELECTIVE IMAGING

RELATED APPLICATIONS

This application is a national stage filing under 35 U.S.C. 371 of International Application PCT/US03/16285, filed May 22, 2003, which claims priority from U.S. Application No. 60/382,524, filed May 22, 2002, the specifications of each of which are incorporated by reference herein. International Application No. PCT/US03/16285 was published under PCT Article 21(2) in English.

GOVERNMENT INTERESTS

The United States Government has certain rights in this invention pursuant to Department of Energy Grant #DE-FG02-01ER63188.

BACKGROUND OF THE INVENTION

A number of medical imaging techniques have emerged for capturing still or moving pictures using dyes that can be safely introduced into living tissue. For example, fluorescent dyes may be adapted for sequestration or preferential uptake at a location of medical interest, such as a lesion. The location may then be exposed to a light source that stimulates fluorescence of the dye to permit visualization that enhances a feature of the location. Other emerging techniques employ phosphorescent, chemoluminescent, or scintillant substances to generate photons at one or more wavelengths suitable for imaging. These techniques have proven useful for medical imaging and surveillance, with applications including lesion imaging, calcium deposit imaging, and blood flow imaging.

Such imaging techniques have been enhanced with simultaneous capture and rendering of visible light images. This may, for example, provide a navigational tool at a surgical site, with the diagnostic image and the visible light image superimposed for improved visualization. Charge-coupled devices ("CCDs") provide one well-known system for converting incident photons, or light, into a measurable electronic charge. As a significant disadvantage, current CCD systems that combine visible light and emission wavelength imaging typically employ commercially available components, and require at least two separate cameras: a first camera to capture the visible light image and a second camera for capturing the diagnostic emission wavelength which is commonly, though by no means exclusively, in the near-infrared range. A two-camera system imposes the cost of an additional camera, as well as optics for splitting the visual light wavelengths from the emission wavelength and directing each to a separate transducer. There is also additional software complexity and processing overhead in order to synchronize and superimpose image data streams from the two cameras.

There remains a need for an integrated device that captures images from visible light wavelengths and diagnostic emission wavelengths.

SUMMARY OF THE INVENTION

An imaging device captures both a visible light image and a diagnostic image, the diagnostic image corresponding to emissions from an imaging medium within the object. The visible light image (which may be color or grayscale) and the diagnostic image may be superimposed to display regions of diagnostic significance within a visible light image. A number of imaging media may be used according to an intended application for the imaging device, and an imaging medium may have wavelengths above, below, or within the visible light spectrum. The devices described herein may be advantageously packaged within a single integrated device or other solid state device, and/or employed in an integrated, single-camera medical imaging system, as well as many non-medical imaging systems that would benefit from simultaneous capture of visible-light wavelength images along with images at other wavelengths.

In one aspect, the system includes a device that captures photon intensity from an illuminated object, the device being exposed to an image through a filter wheel including one or more filters that selectively pass wavelengths of light to form a visible light image of the object and a filter that selectively passes wavelengths of light to form a diagnostic image of the object, the diagnostic image corresponding to emissions from an imaging medium within the object.

In another aspect, the system includes a plurality of devices that capture photon intensity from an illuminated object, the devices being exposed to an image through a beam splitter and filters that selectively pass incident photons along a number of paths according to wavelength, each one of the plurality of devices that capture photon intensity being selectively exposed to an image including wavelengths passed along one of the number of paths, at least one of the paths selectively passing wavelengths to form a diagnostic image of the object, the diagnostic image corresponding to emissions from an imaging medium within the object, and at least one of the paths selectively passing wavelengths to form a visible light image of the object.

In another aspect, the system includes a device that captures photon intensity from an illuminated object at a plurality of pixel locations, each one of the plurality of pixel locations covered by a filter, at least one of the filters selectively passing wavelengths to form a visible light image of the object at a corresponding pixel location and at least one of the filters selectively passing wavelengths of light to form a diagnostic image of the object at a corresponding pixel location, the diagnostic image corresponding to emissions from an imaging medium within the object.

In another aspect, the system includes a device that captures photon intensity from an illuminated object at a plurality of pixel locations, each one of the plurality of pixel locations including a plurality of successive diode junctions formed at the boundary of nested p-type and n-type semiconductor wells, each diode junction selectively detecting incident light over a range of wavelengths, at least one of the diode junctions detecting wavelengths of a visible light image of the object at that pixel location and at least one of the diode junctions detecting wavelengths of a diagnostic image of the object at that pixel location, the diagnostic image corresponding to emissions from an imaging medium within the object.

The device that captures photon intensity may be a charge-coupled device. The device may consist of an integrated circuit. The imaging medium may be a fluorescent dye, a phosphorescent substance, a chemoluminscent substance, and/or a scintillant substance. The imaging medium may be a substance introduced into the object. The imaging medium may be a substance inherently present within the object. The object may be an object within a surgical field. The visible light image may be monochromatic. The visible light image may include red, blue and green wavelengths of light. The visible light image may include cyan, magenta, and yellow wavelengths of light. The diagnostic image may include a near-infrared wavelength. The diagnostic image may include an infrared wavelength. The diagnostic image may include a plurality of diagnostic images, each at a different range of wavelengths. The diagnostic image may be formed from one or more diagnostic wavelengths in the visible light range, the object being illuminated with a light source that is depleted in the diagnostic wavelength range.

The visible light image and diagnostic image may be processed and displayed in a medical imaging system. The medical imaging system may include a display for rendering a composite image including a superposition of the visible light image and the diagnostic image. The medical imaging system may include one or more inputs for controlling at least one of a field of view of the object, a focus of the object, or a zoom of the object. The medical imaging system may include a surgical tool. The visible light image and diagnostic image may be processed and displayed in at least one of a machine vision system, an astronomy system, a military system, a geology system, or an industrial system.

The system may be packaged in a camera. The camera may include a visible light image output, a diagnostic image output, and a combined image output, the combined image output providing a superposition of the visible light image and the diagnostic image. The system may capture moving video, or the system may capture still images.

In another aspect, the system may include a solid state device that captures a visible light image of an object under illumination in digital form and a diagnostic image of the object in digital form, the diagnostic image corresponding to an intensity of emission from an imaging medium within the object.

In another aspect, the system may include a single camera that captures a visible light image of an object under illumination and a diagnostic image of the object, the diagnostic image corresponding to an intensity of emission from the object, the camera configured to provide a digital version of the visible light image and a digital version of the diagnostic image to an external display system.

In another aspect, a method may include the steps of illuminating an object to provide an image; capturing an image of the object that includes a visible light image and a diagnostic image, the diagnostic image corresponding to emissions from an imaging medium within the object; and storing the image.

Capturing an image may include passing the image through a filter wheel that exposes an image capture device to the image through a plurality of filters, at least one of the plurality of filters selectively passing wavelengths of light to form a visible light image of the object and at least one of the plurality of filters selectively passing wavelengths of light to form a diagnostic image of the object. Capturing an image may include passing the image through a beam splitter and filters that selectively pass incident photons along a number of paths according to wavelength and exposing each one of a plurality of devices that capture photon intensity to an image including wavelengths passed along one of the number of paths, at least one of the paths selectively passing wavelengths to form a diagnostic image of the object, and at least one of the paths selectively passing wavelengths to form a visible light image of the object.

Capturing an image may include capturing the image at a plurality of pixel locations, each one of the plurality of pixel locations covered by a filter, at least one of the filters selectively passing wavelengths to form a visible light image of the object at a corresponding pixel location and at least one of the filters selectively passing wavelengths of light to form a diagnostic image of the object at a corresponding pixel location. Capturing the image may include capturing the image at a plurality of pixel locations, each one of the plurality of pixel locations covered by a filter, at least one of the filters selectively passing wavelengths to form a visible light image of the object at a corresponding pixel location and at least one of the filters selectively passing wavelengths of light to form a diagnostic image of the object at a corresponding pixel location. Capturing the image may include capturing the image at a plurality of pixel locations, each one of the plurality of pixel locations including a plurality of successive diode junctions formed at the boundary of nested p-type and n-type semiconductor wells, each diode junction selectively detecting incident light over a range of wavelengths, at least one of the diode junctions detecting wavelengths of a visible light image of the object and at least one of the diode junctions detecting wavelengths of a diagnostic image of the object at that pixel location.

BRIEF DESCRIPTION OF THE DRAWINGS

The invention will be appreciated more fully from the following further description thereof, with reference to the accompanying drawings, wherein.

DETAILED DESCRIPTION OF CERTAIN EMBODIMENTS OF THE INVENTION

To provide an overall understanding of the invention, certain illustrative embodiments will now be described, including an image capture device for simultaneously capturing visible-light and near-infrared images. It will be understood that the methods and systems described herein can be suitably adapted to a range of medical imaging applications where visible light tissue images may be usefully combined with diagnostic image information obtained from other specified wavelengths. For example, the systems may be applicable to a wide range of diagnostic or surgical applications where a target pathology, tissue type, or cell may be labeled with a fluorescent dye or other fluorescent substance. More generally, the systems described herein may be adapted to any imaging application where a visible light image may be usefully enhanced with an image of one or more features that are functionally marked to emit photons outside the visible light range by a dye or other material that emits photons at a known wavelength, either inherently or in response to another known wavelength. The systems may also be employed, for example, in a machine vision system, or in a variety of other military, industrial, geological, astronomical or other imaging systems. These and other applications of the systems described herein are intended to fall within the scope of the invention.

Figure 1:
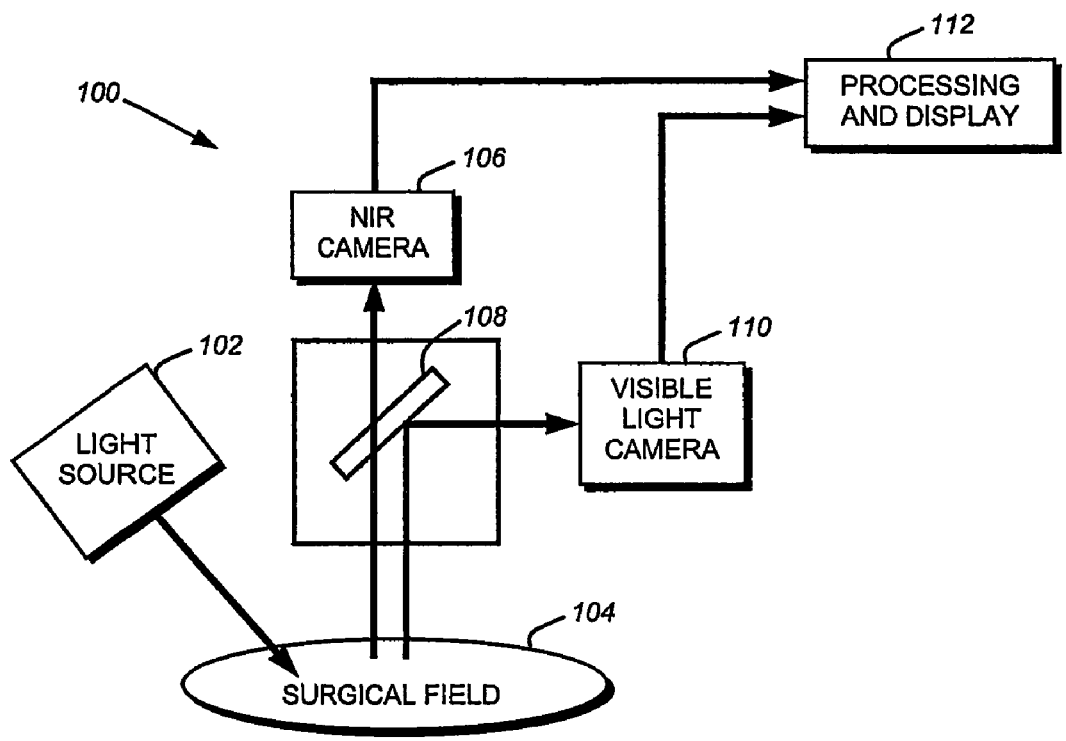
FIG. 1 is a block diagram of a prior art imaging system.

FIG. 1 is a block diagram of a prior art imaging system. The imaging system 100 may include a light source 102 directed at a surgical field 104, a near-infrared camera 106 receiving near-infrared light from the surgical field 104 through a dichroic mirror 108, and a visible light camera 110 receiving visible light reflected from the dichroic mirror 108. A processing and display system 112 receives data from the cameras 106. A dye source (not shown) containing a dye may also be included for introduction into an object in the surgical field 104, such as through injection into the bloodstream of a patient.

The light source 102 may include a visible light source and an excitation light source that illuminate the surgical field 104. Preferably, the light source 102 is depleted in the wavelength region where the dye or other emitting substance emits light, so that the light source 102 does not interfere with a diagnostic image obtained from the dye.

The near-infrared camera 106 captures a diagnostic image from an illuminated object within the surgical field at a wavelength or range of wavelengths that pass through the dichroic mirror 108, while the visible light camera 110 captures a visible light image from the illuminated object within the surgical field. The visible light image may be captured and rendered in a number of manners, such as "RGB" (red-green-blue), "CMY" (cyan-magenta-yellow), or monochromatic grayscale. The diagnostic image corresponds to emissions from the dye or other imaging medium introduced to the object, such that the resulting image is based, for example, upon the distribution of the dye in within the object in the surgical field.

It will be appreciated that visible light typically includes light wavelengths from 400 nm to 700 nm, while near-infrared light may include one or more wavelengths of about 810 nm, or more generally, wavelengths from about 700 nm to about 1000 nm. In other variations, the emission wavelength may be, for example, other near-infrared wavelengths, an infrared wavelength, or a far red wavelength. More generally, the emission wavelength may be any wavelength of emission that can be generated by an imaging medium introduced into an imaging subject and usefully captured for imaging with the devices described herein.

The imaging medium may include, for example, fluorescent dyes that emit in response to a stimulus wavelength, or a substance that emits photons at a known wavelength without stimulus, such as phosphorescent, chemoluminescent, or scintillant substances. As one useful example, fluorescent substances, such as semiconductor nanocrystals (a.k.a. "quantum dots") may be used to emit photons at one or more specific wavelengths, such as infrared wavelengths (e.g., 1320 nm). The imaging medium may include substances inherently present in the object being imaged, such as fluorescent or phosphorescent endogenous biological substances. In certain embodiments, the imaging medium may emit light in a range within the visible light spectrum. This may be usefully employed as a diagnostic imaging source, provided the light source 102 is adequately depleted, such as through filtering, in a corresponding wavelength range so that the light source 102 does not produce reflected light within the diagnostic image wavelength range. The term "imaging medium" as used herein, refers to any of the imaging media described above, or any other medium capable of emitting photons useful in locating regions of functional or diagnostic significance. A "diagnostic image" as that term is used herein, refers to any image formed by detecting emissions from the imaging media described above.

Once captured, each diagnostic image may be shifted to a suitable visible light wavelength for purposes of display. In one embodiment, this pseudo-coloring employs a color specifically selected to provide a substantial color contrast with the object of the visible light image. A color may be selected in advance, such as bright lime green for a diagnostic image over living tissue, or the color may be determined automatically by an algorithm designed to determine average background color and choose a suitable contrasting color. The visible light and diagnostic images may be combined by the image processing and display system 112 and presented on a display where they may be used, for example, by a surgeon conducting a surgical procedure. The processing and display system 112 may include any suitable hardware and software to combine and render the diagnostic and visible light images in any manner useful for a user of the system 100, such as a composite image formed from a superposition of the diagnostic and visible light images, or side-by-side rendering of the diagnostic and visible light images.

The processing and display system 112 may be part of a medical imaging system that also includes, for example, inputs to control visual navigation of the surgical field, such as field of view (e.g., X and Y panning), zoom, and focus, or inputs for controlling a surgical tool associated with the system 100. Similar controls may be provided for the non-medical applications noted above, with certain adaptations as appropriate, such as azimuth and elevation in place of X/Y panning for astronomical applications.

It will be appreciated that certain of the terms and concepts introduced above are applicable to some or all of the embodiments described below, such as the terms diagnostic image and imaging medium, as well as the nature of the processing and display system, except as specifically noted below. It will also be appreciated that adaptations may be made. For example, where a single, integrated camera is provided for capturing both a visible light image and a diagnostic image, some of the image processing for pseudo-coloring the diagnostic image and superimposing the diagnostic image onto the visible light image may be provided by the camera, with an output of the processed image provided in any suitable format to a computer, display, or medical imaging system.

Figure 2:
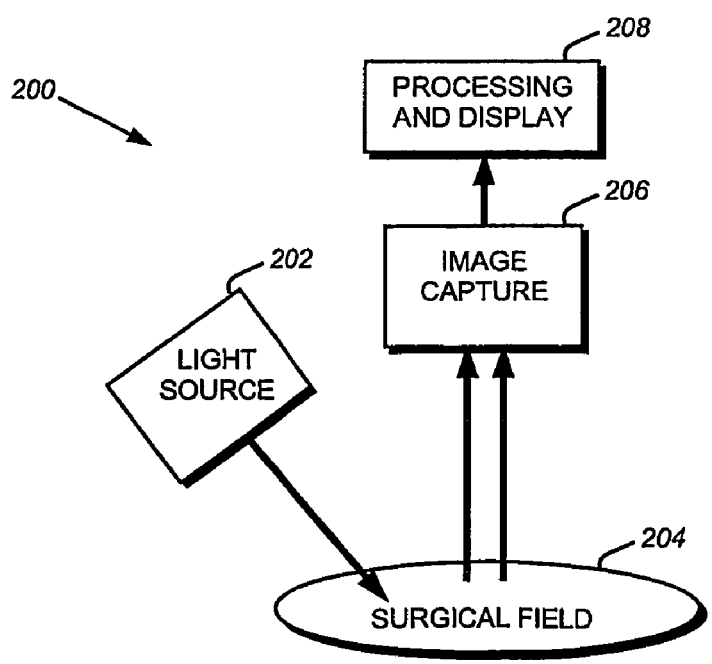
FIG. 2 is a block diagram of an imaging system with an integrated image capture device.

FIG. 2 is a block diagram of an imaging system with an integrated image capture device. The imaging system 200 may include a light source 202 directed at a surgical field 204, an image capture device 206 receiving light from the surgical field 204, and a processing and display system 208. A dye source (not shown) containing in imaging medium such as a dye may also be included for introduction into an object in the surgical field 204, such as through injection into the bloodstream of a patient. The imaging system 200 may be in many respects like the imaging system 100 described above with reference to FIG. 1. It will readily be appreciated that the imaging system 200 differs in at least one respect—the use of a single image capture system 206.

The system 200 advantageously incorporates visible light and diagnostic wavelength imaging into a single device, the image capture system 206. This removes the need for additional external hardware, such as the dichroic mirror 108 of FIG. 1, or additional hardware and/or software in the processing and display system 208 to perform additional processing for images from two separate image capture devices, which processing may range from image registration to matching of frame rates, image sizes, and other features of images from disparate cameras. The image capture system 206 may be packaged as a single solid state device suitable for integration into a larger system, or as a camera with inputs for remote operation and/or outputs including a visible light output, a diagnostic image output, and a combined output that superimposes the diagnostic and visible light images.

In certain embodiments, the image capture system 206 may provide for capture of two or more wavelengths of diagnostic significance through adaptations of the systems described below. Thus two or more diagnostic images may be displayed, and/or superimposed on a visible light image in order to simultaneously visualize two or more features or characteristics of interest. The image capture system 206 may provide still images, or may provide moving images, such as in a real-time display of a surgical field.

A number of technologies may be suitable adapted to the image capture system 206. Charge-Coupled Devices ("CCDs"), for example, are known for use in capturing digital images. These devices may be fabricated on silicon substrates and packaged as chips, employing various CCD technologies. For example, full-frame-transfer ("FF") and frame-transfer ("FT") devices employ MOS photocapacitors as detectors, while interline transfer ("IL") devices use photodiodes and photocapacitors for each detector. These architectures are among the more commonly employed architectures in current CCD cameras. Each CCD technology has its own advantages and disadvantages, resulting in trade-offs between, for example, cost, design complexity, and performance. These technologies are generally adaptable to the systems described herein, and carry with them the corresponding design trade-offs, as will be appreciated by those of skill in the art.

Other image-sensing architectures using charge-coupled devices are known, and may be usefully employed with the systems described herein, including frame-interline transfer devices, accordion devices, charge injection devices, and MOS X,Y addressable devices. All such devices are intended to fall within the meaning of "charge-coupled device" as that term is used herein. While all of these devices are useful for converting incident photons into measurable electronic charges, they are inherently monochromatic in nature. As such, color-imaging applications have been devised for these CCDs that selectively image different wavelengths. These techniques for wavelength selection may be adapted to the present system as described in greater detail below.

Figure 3:
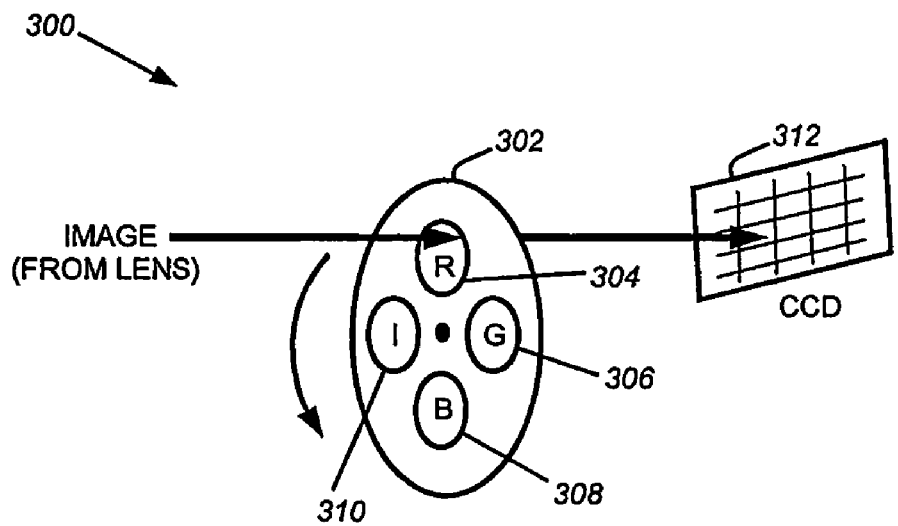
FIG. 3 depicts an embodiment of an image capture device.

FIG. 3 depicts an embodiment of an image capture device. The device 300 applies an adaptation of mechanical color wheels used for some conventional red-green-blue ("RGB") imaging systems. A image of an illuminated object may be focused through a lens and captured in four successive exposures, each synchronized with a filter wheel 302 having desired optical characteristics. In the depicted embodiment, this includes a red filter 304 that selectively passes red light, a green filter 306 that selectively passes green light, a blue filter 308 that selectively passes blue light, and a near-infrared filter 310 that selectively passes near-infrared light. The CCD 312 is exposed to the image through the red, green, and blue filters 304, 306, 308 collectively to capture a visible light image, and exposed to the image through the near-infrared filter 310 that selectively passes near-infrared emissions to capture a diagnostic image of interest, such as emission from a fluorescent dye.

Each exposure of the CCD 312 is sequentially read into data storage (not shown) where it can be reconstructed into a complete image. It will be appreciated that a number of other wavelengths may be selectively passed by the fourth filter to obtain a diagnostic image of the object, including infrared wavelengths or other wavelengths of interest, as generally described above. It will further be appreciated that additional filters may be added to the color wheel so that two or more emission wavelengths may be captured within the same image. Thus a color wheel with five or more filters is contemplated by the systems described herein.

In another aspect, a method according to the above system may include capturing an image that passes through the filter wheel 302 on the CCD 312 or other image capture device to obtain a visible light image and a diagnostic image.

Figure 4:
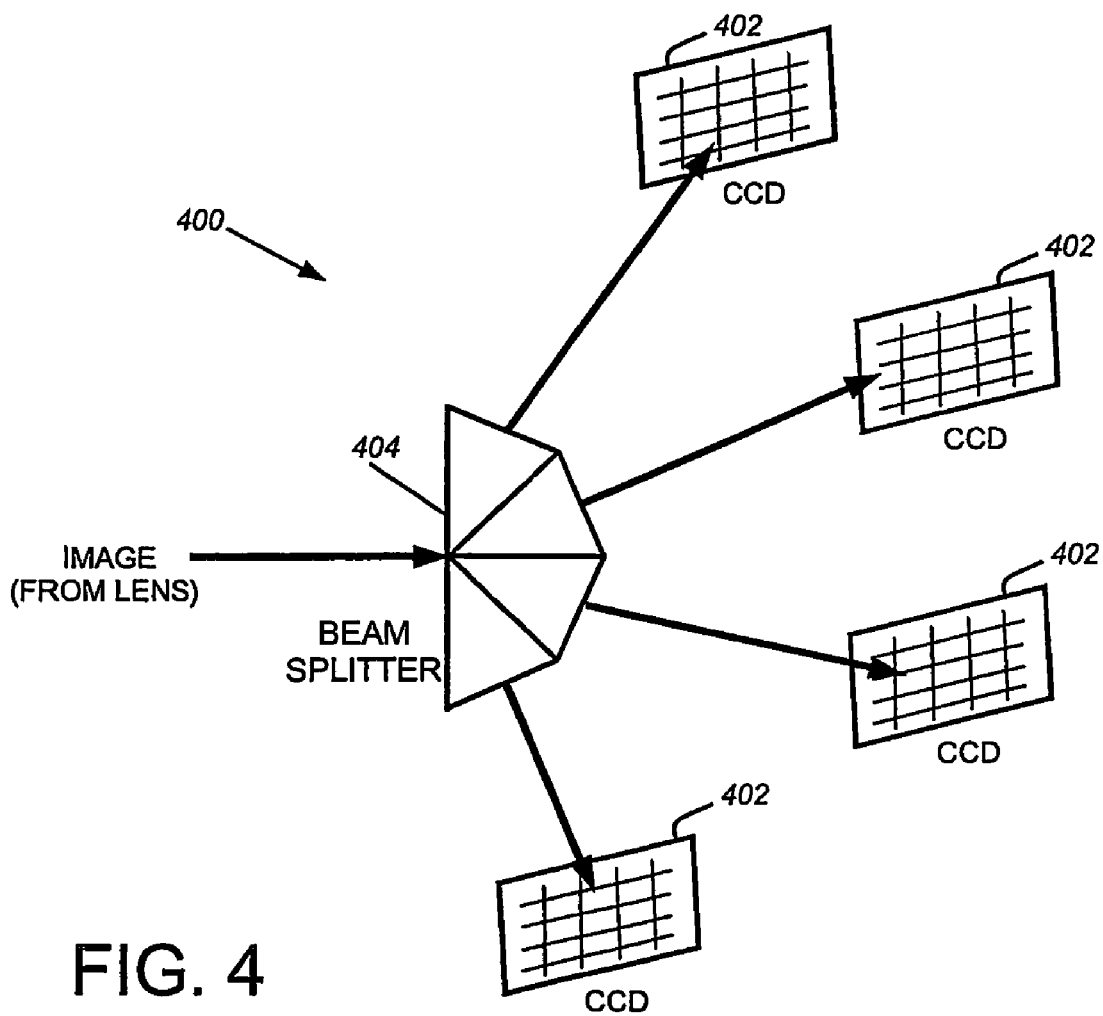
FIG. 4 depicts an embodiment of an image capture device.

FIG. 4 depicts an embodiment of an image capture device. As shown in the figure, a multi-chip device 400 may employ optics to split an image into separate image planes. A focused image is provided to the device 400, such as by passing an image of an illuminated object through a lens. A plurality of CCDs 402 or other image capture devices for measuring photon intensity are exposed to the image through a beam splitter 404, with a CCD 402 placed in each image plane exiting the beam splitter 404. A filter may also be provided for each CCD 402 to selectively expose the CCD 402 to a range of wavelengths, so that the image is selectively passed along a number of paths according to wavelengths. It will be appreciated that other similar approaches may be used to apply differing wavelengths to a collection of CCDs 402 in a multichip CCD system, such as a prism or a wavelength separating optical device or devices. In such systems, the CCDs 402 may be operated synchronously to capture different incident wavelengths at or near the same point in time.

In FIG. 4, the beam-splitter 404 provides four different CCDs 402, a first CCD with a filter that passes red light, a second CCD with a filter that passes green light, a third CCD with a filter that passes blue light, and a fourth CCD with a filter that passes near-infrared light. The first three CCDs produce a visible light image, while the fourth CCD produces a diagnostic image according to an imaging medium introduced into the object. However, It will be appreciated that other wavelengths may be passed by the fourth filter, including infrared wavelengths or other wavelengths of interest. It will further be appreciated that additional light paths may be provided by the beam splitter with additional filtered CCDs for each path, so that two or more emission wavelengths may be captured within the same image. Thus a system with five or more CCDs is contemplated by the systems described herein.

In another aspect, a method according to the above system may include capturing an image that passes through the beam splitter 404 and filters that selectively pass incident photons along a number of paths according to wavelength, with each CCD (or other image capture device) capturing either a visible light image or a diagnostic image of the illuminated object.

Figure 5:
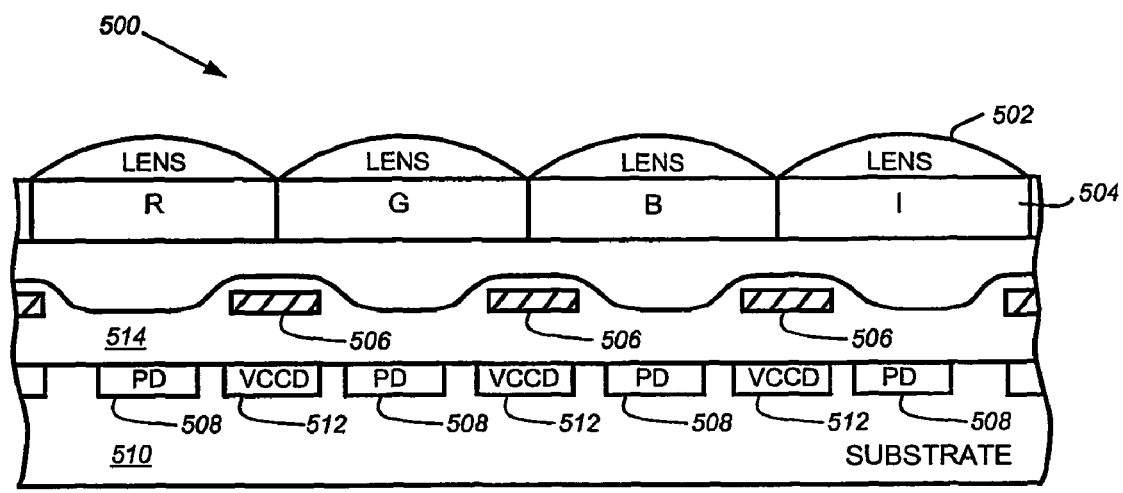
FIG. 5 is a side view of an image capture device on a single, integrated semiconductor device.

FIG. 5 is a side view of an image capture device on a single, integrated semiconductor device. The figure shows a CCD array 500 with wavelength selection using an integral filter array. The CCD array 500 may include lenses 502, a filter array 504, gates 506, photodiodes 508, a substrate 510, vertical charge-coupled devices ("VCCDs") 512, and an insulation layer 514.

In the CCD array 500, the photodiodes 508 serve to detect the intensity of incident photons at pixel locations within a focused image, while the filter array 504 with appropriate characteristics are arranged over the photodiodes 508 such that different photodiodes are exposed to different wavelengths of incident light. The filter array 504 may include, for example red filters that selectively pass red wavelengths (labeled "R"), green filters that selectively pass green wavelengths (labeled "G"), blue filters that selectively pass blue wavelengths (labeled "B"), and near-infrared filters that selectively pass near-infrared wavelengths (labeled "I"). The VCCDs 512 may be formed vertically between the photodiodes 508 for transferring signals produced by photoelectric conversion in the photodiodes 508. The insulation layer 514 may be formed over the entire surface of the semiconductor substrate 510 (including the photodiodes 508 and the VCCD 512), and the plurality of gates 506 may be formed on the insulation layer 514 above each VCCD 512 for controlling the transfer of the photodiode signals. A metal shielding layer for shielding light may be deposited over the gates 512, except for the light-receiving regions of the photodiodes 508. A flat insulation film may then be deposited over the entire surface of the semiconductor substrate including the metal shielding layer.

The filter array 504, which passes either red ("R"), green ("G"), blue ("B") (collectively for forming a visible light image), or near-infrared ("NI") wavelengths (for a diagnostic image) may then be formed over each photodiode 508 corresponding to a pixel to be imaged from an illuminated object. A top coating layer may be deposited on the filter layer 504. Finally, a lens 502 may be formed on the top coating layer for concentrating photons on each photodiode.

The filter array 504 separates the spectrum of incident light to selectively pass only the light of a predetermined wavelength, or range of wavelengths, to reach each of the photodiodes. The metal shielding layer restricts incident light to the photodiodes 508. The incident light is converted into an electric signal in the photodiodes 508, and transferred out to a processor under control of the gates 506.

The filter array 504 may be dyed or otherwise masked or processed so that each photodiode 508 is exposed to a specific wavelength or range of wavelengths. It will be appreciated that the device of FIG. 5 is an example only, and that a number of different CCD topologies may be used with an integral filter array 504, and may be suitably adapted to the systems described herein. It should also be appreciated that other photoactive substances may be included in place of, or in addition to, the filters in the filter array 504, in order to enhance response at certain wavelengths, or to affect a shift in wavelength to a more suitable frequency for measurement by the photodiodes. All such variations are intended to fall within the scope of this description.

Figure 6:
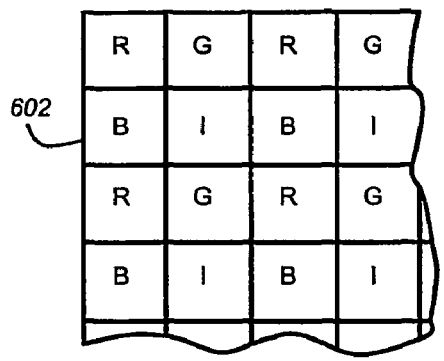
FIG. 6 is a top view of an image capture device on a single, integrated semiconductor device.

FIG. 6 is a top view of an image capture device on a single, integrated semiconductor device. The figure depicts one possible arrangement of filters 602 for use with the systems described herein. In this integral filter array 602, four filters are arranged to expose photodiodes to red (labeled "R"), green (labeled "G"), blue (labeled "B"), and near-infrared (labeled "I") wavelengths. Each two-by-two group of photodiodes may form a pixel, with four wavelength measurements being detected for that pixel at different photodiodes.

It will be appreciated that a number of other wavelengths may be passed by the fourth filter ("I"), including infrared wavelengths or other wavelengths of interest. It will further be appreciated that additional filters may be disposed upon the CCD, with suitable adjustments to the arrangement of filters, so that two or more emission wavelengths may be captured within the same image. Thus a system with an integral filter for five or more wavelengths is contemplated by the systems described above.

In another aspect, a method according to the above system may include capturing an image that passes through a filter array that selectively passes wavelengths of either a visible light image or a diagnostic image to a pixel location in a charge coupled device.

Figure 7:
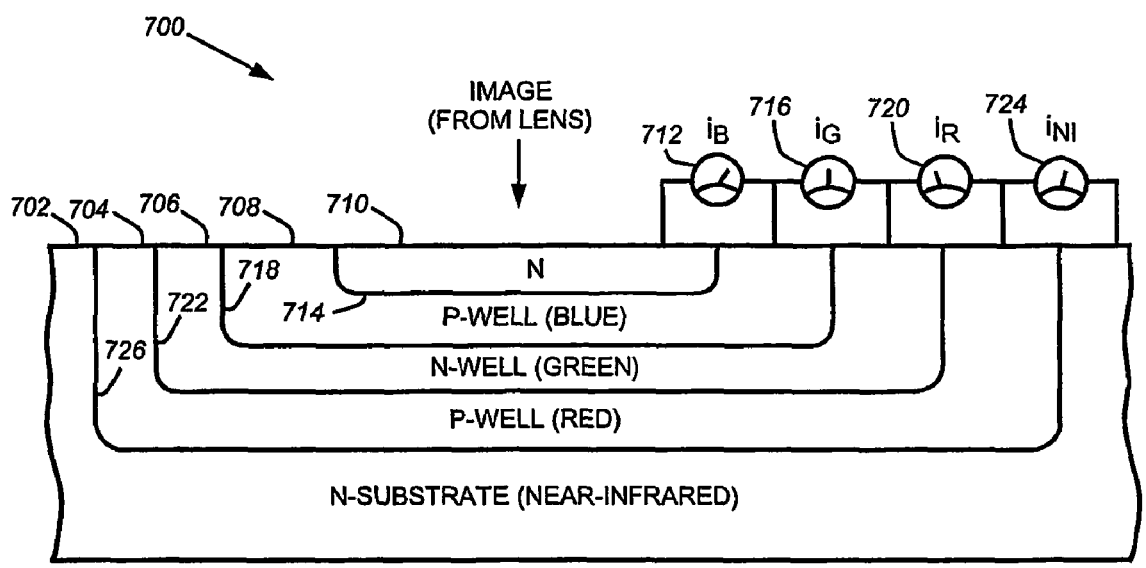
FIG. 7 is a side view of an image capture device on a single, integrated semiconductor device.

FIG. 7 is a side view of an image capture device on a single, integrated semiconductor device. As shown in the figure, the device 700 may include a number of nested p-type and n-type wells, with a p-n diode junction formed at each well boundary that is sensitive to incident photons of a particular wavelength range. By measuring current across these p-n junctions while the device 700 is exposed to light, photon intensity over a number of contiguous wavelengths may be detected at the same location at the same time.

More specifically, the device 700 includes an n-type substrate 702, a p-well 704 within the n-type substrate, an n-well 706 within the p-well 704, a p-well 708 within the n-well 706, and an n-drain 710 within the p-well 708. A first detector 712 measures photocurrent across a first p-n junction 714 and is generally sensitive to blue wavelengths. A second detector 716 measures photocurrent across a second p-n junction 718, and is generally sensitive to green wavelengths. A third detector 720 measures photocurrent across a third p-n junction 722, and is generally sensitive to red wavelengths. A fourth detector 724 measures photocurrent across a fourth p-n junction 726, and is generally sensitive to an emission wavelength from an imaging medium within an object.

A similar, triple-well structure is described, for example, in U.S. Pat. No. 5,965,875 to Merrill. In general, such a device operates on the principle that photons of longer wavelengths will penetrate more deeply into silicon before absorption. By alternately doping wells for p-type or n-type conductivity, a number of successive photodiodes are created at the p-n junctions of successive layers, each being sensitive to progressively longer wavelengths of photon emissions. Using well-known active pixel technology to sense photocurrents from these diodes (as shown by circuits labeled "iB", "iG", "iR", and "iNI"), each active pixel region senses photocharge by integrating the photocurrent on the capacitance of a photodiode and the associated circuit node, and then buffering the resulting voltage through a readout amplifier. A shallow, n-type, lightly-doped drain above the first p-type well may be employed to maximize blue response in the first photodiode.

The above quadruple-well system may be advantageously adapted to imaging systems where an emission wavelength is adjacent to, or nearly adjacent to, the visible light spectrum. The near-infrared spectrum, for example, is adjacent to the red wavelength spectrum, and may be measured with the device described above.

In another aspect, a method according to the above system may include capturing photon intensity from an illuminated object at a pixel location at a number of different wavelengths by measuring photocurrent at a plurality of successive diode junctions formed at the boundary of successively nested p-type and n-type semiconductor wells.

The near-infrared spectrum lies in a range that is particularly useful for certain medical imaging applications, due to the low absorption and autofluorescence of living-tissue components in this range. Within a range of 700 nm to 900 nm, the absorbances of hemoglobin, lipids, and water reach a cumulative minimum. This so-called "near-infrared window" provides a useful spectrum for excitation and emission wavelengths in living-tissue imaging applications, and a number of fluorescent dyes using these wavelengths have been developed for medical imaging applications. Thus the quadruple-well device described above not only employs a convenient range of wavelengths adjacent to visible light, it accommodates a number of dyes that are known to be safe and effective for tissue imaging, such as the IR-786 or the carboxylic acid form of IRDye-78, available from LI-COR, Inc.

It will be appreciated that each of the systems described above presents trade-offs in terms of cost, speed, image quality, and processing complexity. For example, the single-CCD filter wheel may introduce significant time delays between different wavelength images, and may not perform well in high-speed imaging applications. By contrast, the multi-chip approach requires more CCD elements and additional processing in order to maintain registration and calibration between separately obtained images, all of which may significantly increase costs. As such, different applications of the systems described herein may have different preferred embodiments.

The systems described above have numerous surgical applications when used in conjunction with fluorescent dyes. For example, the system may be deployed as an aid to cardiac surgery, where it may be used intraoperatively for direct visualization of cardiac blood flow, for direct visualization of myocardium at risk for infarction, and for image-guided placement of gene therapy and other medicinals to areas of interest. The system may be deployed as an aid to oncological surgery, where it may be used for direct visualization of tumor cells in a surgical field or for image-guided placement of gene therapy and other medicinals to an area of interest. The system may be deployed as an aid to general surgery for direct visualization of any function amenable to imaging with fluorescent dyes, including blood flow and tissue viability. In dermatology, the system may be used for sensitive detection of malignant cells or other skin conditions, and for non-surgical diagnosis of dermatological diseases using near-infrared ligands and/or antibodies. More generally, the CCD systems described herein may be used as imaging hardware in conjunction with open-surgical applications, and may also be integrated into a laparoscope, an endoscope, or any other medical device that employs an imaging system. The systems may have further application in other non-medical imaging systems that combine visible light and non-visible light imaging.

In various embodiments, the system described herein includes a wavelength-selective solid state device, such as a CCD or other semiconductor device, a semiconductor chip that includes the solid state device, a camera employing the solid state device, an imaging system employing the solid state device, and methods of imaging that employ the solid state device. A camera using the imaging devices described above may include a lens, user inputs or a wired or wireless remote control input, the imaging device, processing to filter, store and otherwise manage captured images including functions such as superposition of diagnostic and visible light images and pseudo-coloring of the diagnostic image, and one or more outputs for providing the images to a remote device or system.

It will be appreciated that certain imaging technologies are more suitable to capturing certain wavelengths, including technologies such as gas photodiode or microplasma photodetectors, and certain substances or combinations of substances, such as Indium, Gallium, or Germanium may provide enhanced responsiveness over certain wavelength ranges. Some of these are consistent with CMOS manufacturing and may be realized directly on a wafer with visible-light-imaging circuitry and other processing circuitry, or manufactured with micro-electro-mechanical systems technology and packaged within the same chip as related circuitry, or the solid state system may be provided as a chipset that is assembled and provided on a suitable circuit board. All such technologies as may be useful for visible light imaging and/or diagnostic imaging over the wavelengths described above may be used for the solid state devices described above, and are intended to fall within the scope of the invention.

As a significant advantage, cameras using the devices described herein may receive an image through a single lens, and provide both visible light and diagnostic images on a single output. As another significant advantage, visible light and diagnostic images may be obtained from a single, solid-state device, reducing the requirement for moving parts, additional lenses and expensive optics, and post-processing associated with combining images from different sources.

While medical imaging applications have been described, it will be appreciated that the principles of the systems described above may be readily adapted to other applications, such as machine vision or a variety of other military, industrial, geological, astronomical or other imaging systems. For example, a machine vision system may employ a fluorescent dye that selectively adheres to surfaces of a certain texture, or aggregates in undesirable surface defects. A diagnostic image of the dye may assist in identifying and/or repairing these locations.

Thus, while the invention has been disclosed in connection with the preferred embodiments shown and described in detail, various modifications and improvements thereon will become readily apparent to those skilled in the art. It should be understood that all matter contained in the above description or shown in the accompanying drawings shall be interpreted as illustrative, and not in a limiting sense, and that the invention should be interpreted in the broadest sense allowable by law.

The invention claimed is:

1. A system comprising:
a solid state device that captures photon intensity from an illuminated object at a plurality of pixel locations, each one of the plurality of pixel locations including a plurality of successive diode junctions formed at the boundary of nested p-type and n-type semiconductor wells, each diode junction selectively detecting incident light over a range of wavelengths, wherein at least three of the diode junctions detect wavelengths of visible light from the object at that pixel location, thereby providing a visible light image having three color components, and a fourth one of the diode junctions monochromatically detecting an intensity of infrared wavelengths from the object at that pixel location, thereby providing a diagnostic image, the diagnostic image corresponding to emissions from an imaging medium within the object;
an image processing system configured to pseudocolor the diagnostic image to provide a pseudocolored diagnostic image, and configured to superimpose the pseudocolored diagnostic image onto the visible light image to provide a processed image; and
a camera containing a lens, the solid state device, and the image processing system, the camera further including a plurality of inputs for remote operation of the camera and plurality of outputs for an external display system, the plurality of outputs including a visible light output for the visible light image, a diagnostic image output for the diagnostic image, and a combined output for the processed image.

2. The system of claim 1, wherein the imaging medium is at least one of a fluorescent dye, a phosphorescent substance, a chemoluminscent substance, or a scintillant substance.

3. The system of claim 1, wherein the imaging medium is a substance introduced into the object.

4. The system of claim 1, wherein the imaging medium is a substance inherently present within the object.

5. The system of claim 1, wherein the object is an object within a surgical field.

6. The system of claim 1, wherein the visible light image includes red, blue and green wavelengths of light.

7. The system of claim 1, wherein the visible light image includes cyan, magenta, and yellow wavelengths of light.

8. The system of claim 1, wherein the diagnostic image includes a near-infrared wavelength.

9. The system of claim 1, wherein the diagnostic image includes a plurality of diagnostic images, each at a different range of wavelengths.

10. The system of claim 1, wherein the diagnostic image is formed from one or more diagnostic wavelengths in the visible light range, the object being illuminated with a light source that is depleted in the diagnostic wavelength range.

11. The system of claim 1, wherein the visible light image and diagnostic image are processed and displayed in a medical imaging system.

12. The system of claim 1, wherein the medical imaging system includes a display for rendering a composite image including a superposition of the visible light image and the diagnostic image.

13. The system of claim 1, wherein the medical imaging system includes one or more inputs for controlling at least one of a field of view of the object, a focus of the object, or a zoom of the object.

14. The system of claim 1, wherein the medical imaging system includes a surgical tool.

15. The system of claim 1, wherein the visible light image and diagnostic image are processed and displayed in at least one of a machine vision system, an astronomy system, a military system, a geology system, or an industrial system.

16. The system of claim 1, wherein the system captures moving video.

17. The system of claim 1, wherein the system captures still images.

18. The system of claim 1 further comprising a visible light source.

19. The system of claim 18 wherein the visible light source is depleted such that the visible light source does not interfere with the diagnostic image.

20. The system of claim 1 further comprising an excitation light source.

\* \* \* \* \*